United States Patent [19]

Hill

[11] 4,270,627

[45] Jun. 2, 1981

[54] STETHOSCOPE WITH PROBE SOUND PICK-UP AND RESONANT CAVITY AMPLIFICATION

[76] Inventor: Raymond R. Hill, 300 Diogenes Dr., Angwin, Calif. 94508

[21] Appl. No.: 53,924

[22] Filed: Jul. 2, 1979

[51] Int. Cl.³ .......................... A61B 7/02; H04R 25/00
[52] U.S. Cl. .................................... 181/131; 181/137
[58] Field of Search ............... 181/132, 131, 135, 137; 179/15 T, 181 R

[56] References Cited

U.S. PATENT DOCUMENTS

| 2,158,764 | 5/1939 | Silka | 181/137 |
| 2,389,868 | 11/1945 | Olson | 181/131 |
| 2,513,827 | 4/1950 | Tynan | 181/131 |
| 3,157,246 | 11/1964 | Howell | 181/137 |
| 3,179,204 | 4/1965 | Cefaly | 181/137 |

FOREIGN PATENT DOCUMENTS 1030957  5/1966  United Kingdom .

OTHER PUBLICATIONS

Scientific American "The Medical Influence of the Stethoscope", by S. J. Reiser, vol. 240, No. 2, Feb. 1979, pp. 148-155.

Primary Examiner—L. T. Hix
Assistant Examiner—Benjamin R. Fuller
Attorney, Agent, or Firm—Limbach, Limbach & Sutton

[57] ABSTRACT

A stethoscope having one or more resonant cavities adjusted to amplify sound frequencies of interest, such as those of the heart or lungs of a patient, and including a pick-up head that contacts the patient through a probe.

24 Claims, 12 Drawing Figures

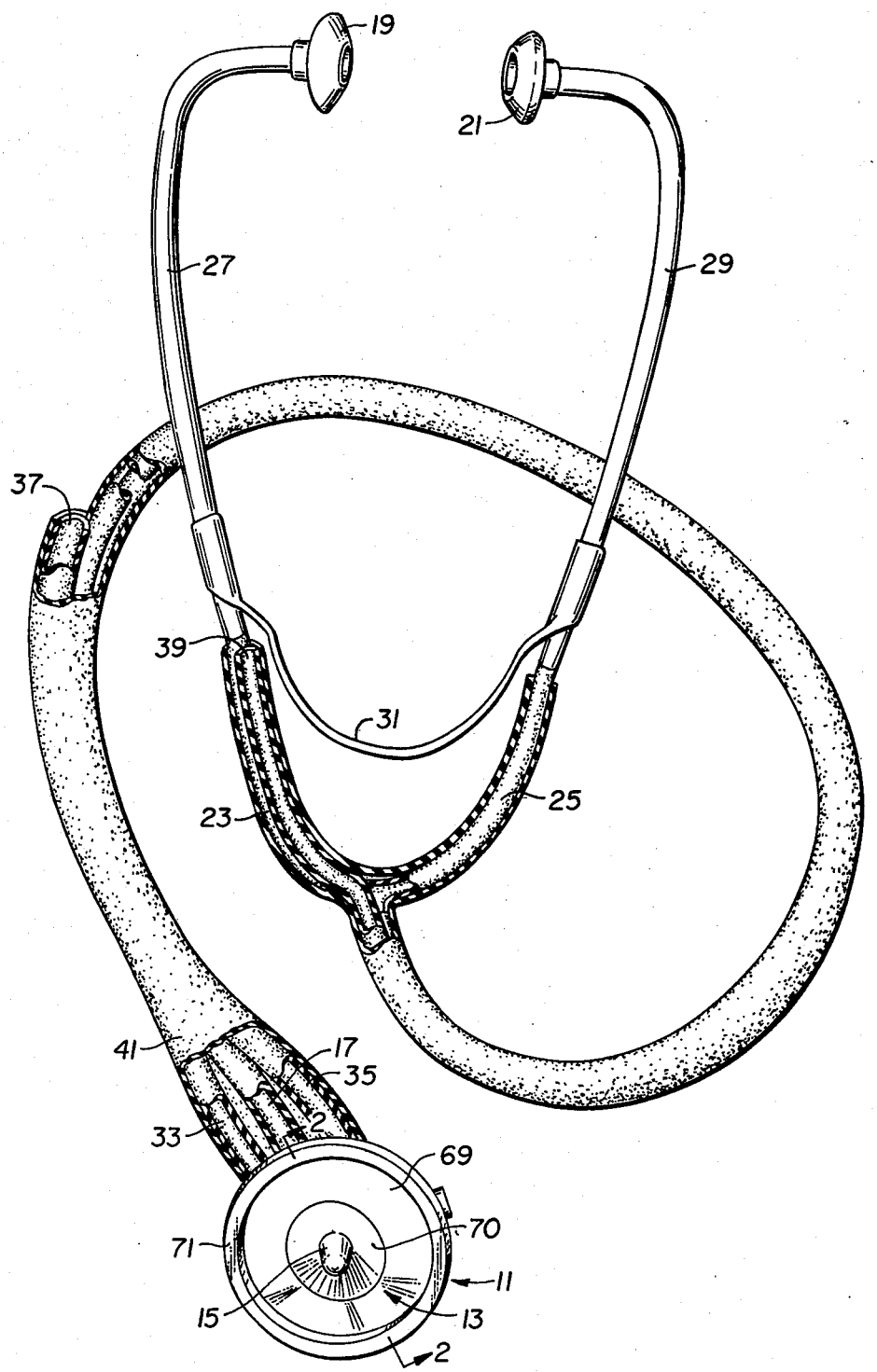
FIG._1.

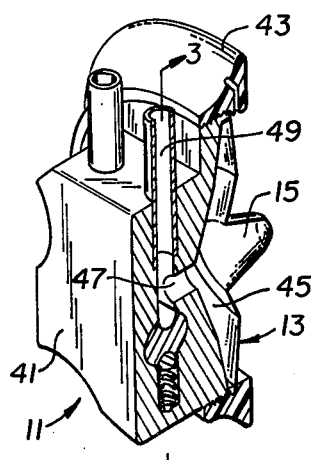
FIG._2.
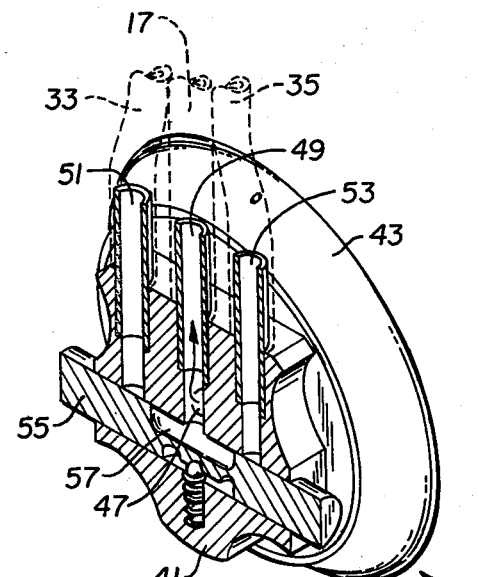
FIG._3A.
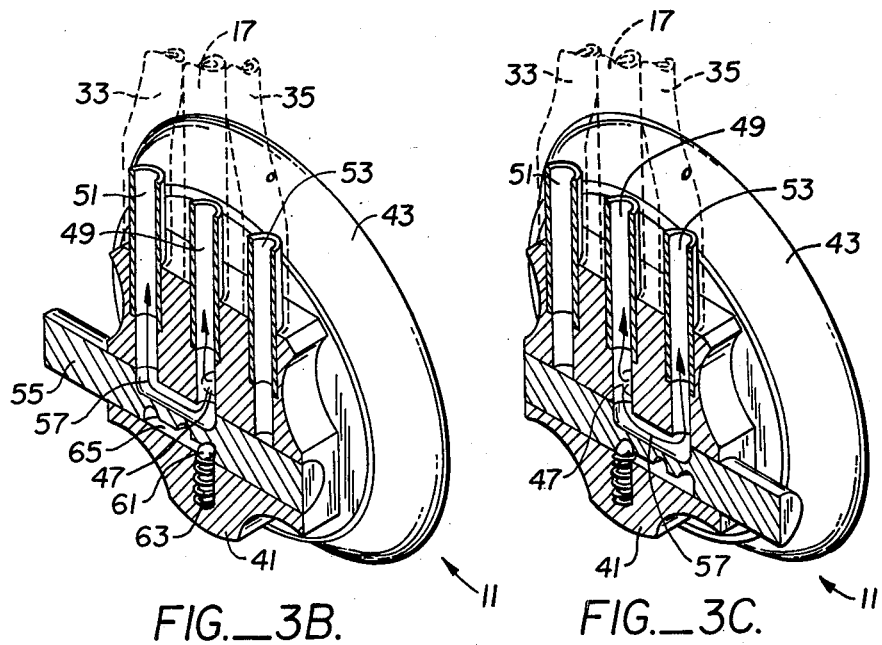
FIG._3B.       FIG._3C.

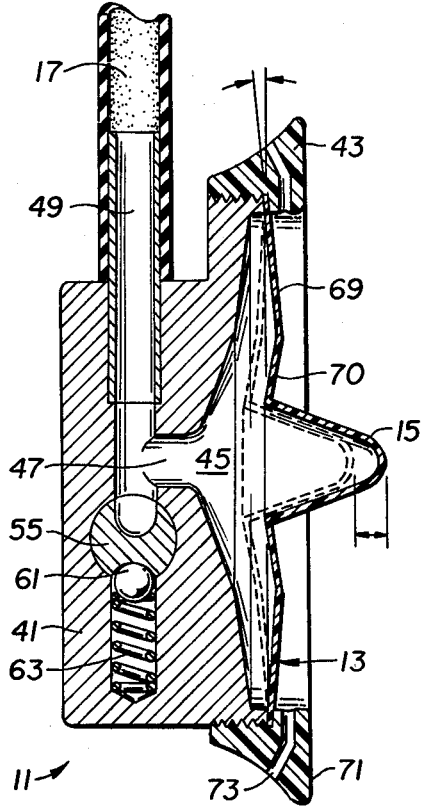
FIG._4A.
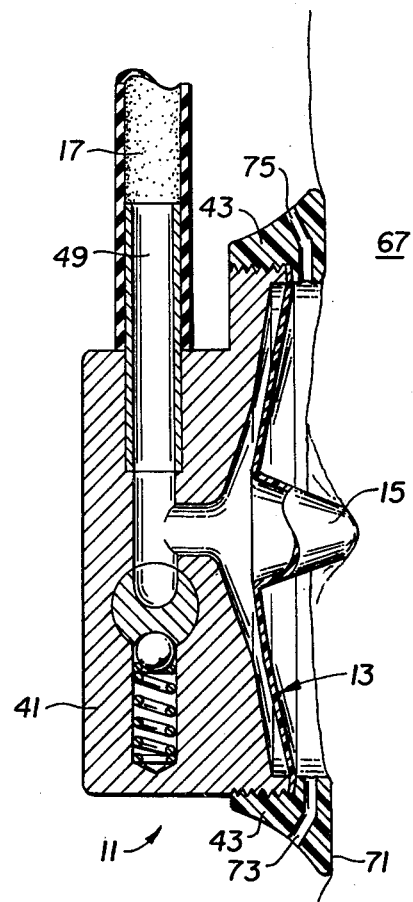
FIG._4B.
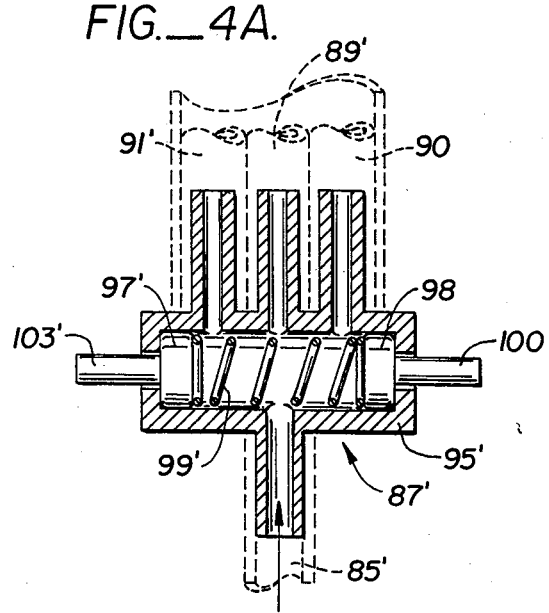
FIG._7.

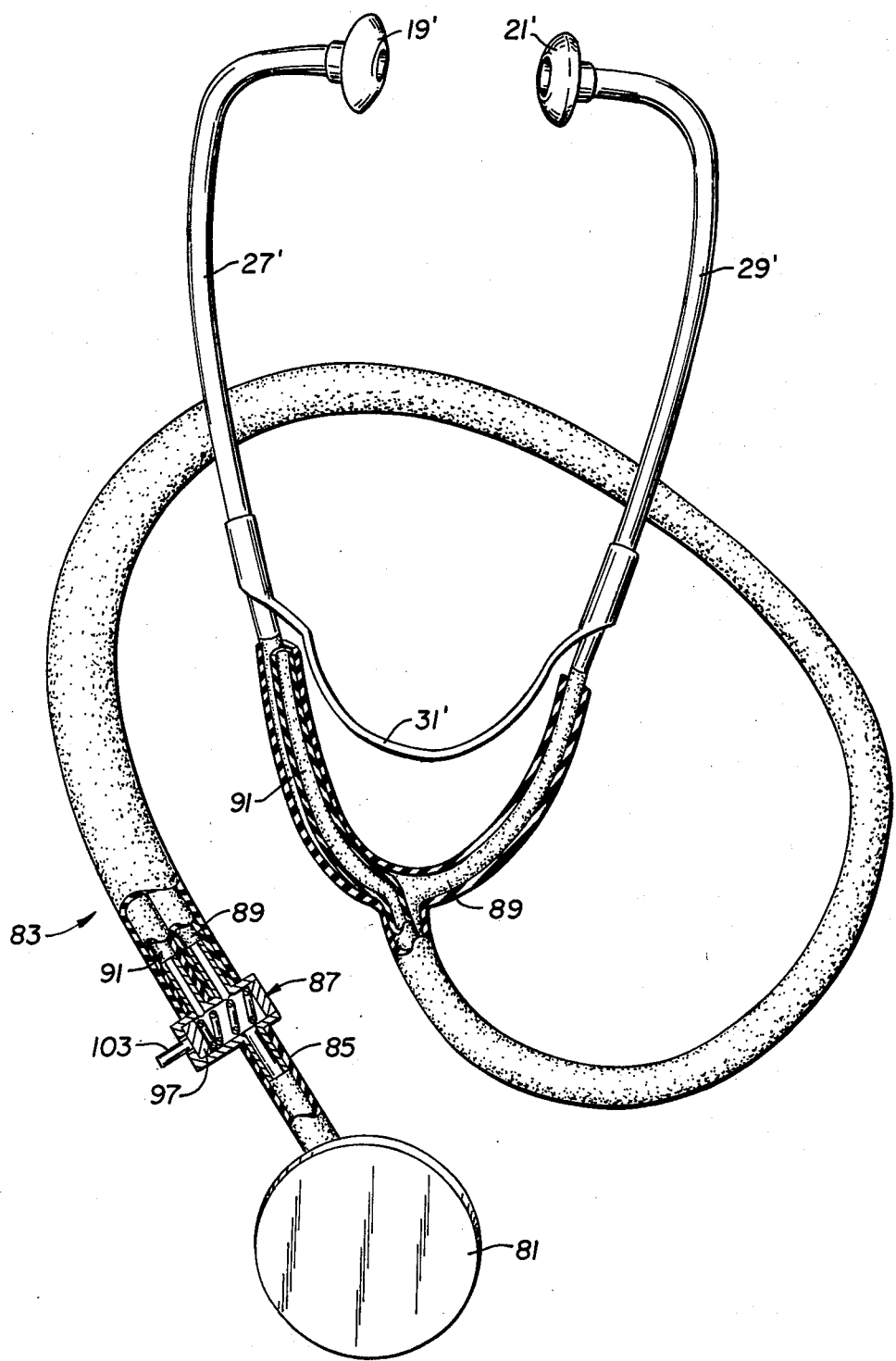
FIG._5.

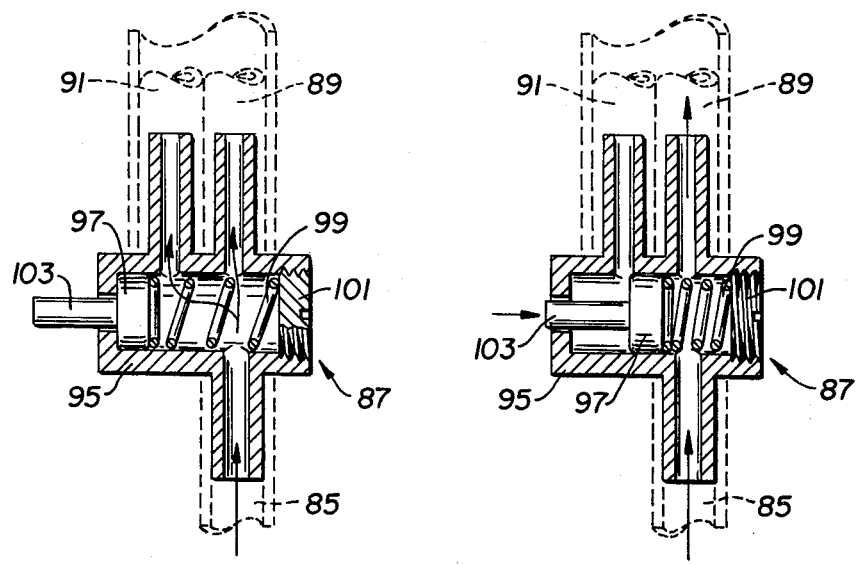
FIG._6A.  FIG._6B.
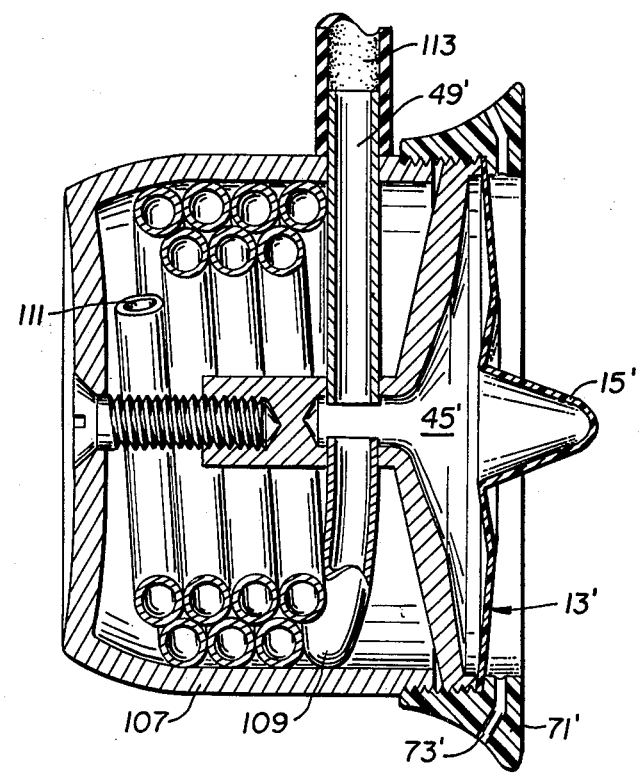
FIG._8.

STETHOSCOPE WITH PROBE SOUND PICK-UP AND RESONANT CAVITY AMPLIFICATION

BACKGROUND OF THE INVENTION

This invention relates to stethoscopes and principally to improvements therein for increased amplitude and quality of monitored sounds.

The stethoscope has been a basic tool of medical diagnosis from since the early past of the Nineteenth Century. The history of the stethoscope has been outlined in a recent article, *Scientific American*, February, 1979, beginning at page 148. Despite numerous advances in the electronic medical and clinical diagnostic equipment, the stethoscope remains to be a widely used instrument.

It is a principal object of the present invention to provide an improved stethoscope wherein the user can hear patient's sounds of interest with improved clarity and volume.

SUMMARY OF THE INVENTION

This and additional objects are accomplished by the various aspects of the present invention wherein, briefly, one or more air cavities are added to an existing stethoscope of a size to be resonant at the predominant range of frequencies of interest in order to increase the volume of these frequencies. Additionally, an improved sound pick-up head is provided that utilizes a probe attached to a diaphragm, the probe contacting the patient for picking up sounds, resulting in improved clarity.

Other objects, advantages and features of the various aspects of the present invention will become apparent from the following description of a preferred embodiment thereof, which description should be taken in conjunction with the accompanying drawings.

BRIEF DESCRIPTION OF THE DRAWINGS

FIG. 1 shows a stethoscope incorporating the resonant cavity and pick-up head improvements of the present invention;

FIG. 2 is a cutaway view of a portion of the stethoscope of FIG. 1 taken at section 2—2;

FIGS. 3A, 3B and 3C show three operable positions of an element of the improved stethoscope of FIG. 1 as viewed from section 3—3 of FIG. 2;

FIGS. 4A and 4B illustrate the operation of another element of the improved stethoscope of FIG. 1 taken at section 2—2 thereof;

FIG. 5 shows another embodiment of the present wherein the resonant cavity improvement is incorporated into an existing stethoscope;

FIGS. 6A and 6B illustrate in cross-section the operation of a valve of the embodiment of FIG. 5;

FIG. 7 shows a variation of the embodiment of FIGS. 5, 6A and 6B; and

FIG. 8 shows in cross-section yet another embodiment of a pick-up head with resonant cavity according to the present invention.

DESCRIPTION OF A PREFERRED EMBODIMENT

Referring initially to FIG. 1, the basic elements of the improved stethoscope will be described. A sound pick-up head 11 includes a diaphragm 13 stretched thereacross with a probe 15 attached to its center and extending outward of the pick-up head 11 for contacting a patient and being vibrated in accordance with sounds within the patient. These sounds cause the diaphragm 13 to vibrate for communicating the sounds through a tube 17 to ear pieces 19 and 21. The tube 17 splits into two tubes 23 and 25, as in existing stethoscopes, for communicating sound to hollow metal conduits 27 and 29, respectively. Also as in existing stethoscopes, a spring support piece 31 is connected between the metal tubes 27 and 29 for applying pressure of the ear pieces 19 and 21 to the wearer's ears when in use. As in existing stethoscopes, the hollow tubular sound carrying air passage 17 is communicated with the ear pieces 19 and 21 without any interruption, blockage or opening therein outside of the pick-up head 11.

The improved stethoscope of the present invention includes a first resonant cavity 33 and a second resonant cavity 35 which are selectively connected to the sound passage 17 on the back of the pick-up head 11, as described hereinafter. Each of the resonant cavities 33 and 35 is a hollow flexible tube of differing lengths. The cavity 33 is a tube which ends and is open to the atmosphere at a position 37. The tube 35 is longer and ends at a position 39 by opening into the atmosphere. A sheath 41 conveniently wraps around all three tubes 17, 33 and 35 to give an aesthetic appearance.

The resonant cavity tubes 33 and 35 have a length to maximize amplification of the sound frequencies within two sound frequency ranges of interest. The shorter tube 33 is shown in this embodiment to be in the range of from seven to nine inches long measured between the point of its connection to the passage 17 and its end 37. This has been found to maximize lung sounds. The tube 35, designed to maximize sounds from the heart of a patient, is preferably made of the length from two to three feet. In both cases, tubing with an inside diameter of approximately 5/32 inch is preferred. However, it will be recognized that other forms and shapes of resonant cavities could be utilized but the tubing does have the advantage of being simple, economical and easily adaptable to existing stethoscope designs.

The use of resonant cavities according to the present invention has a further advantage, in addition to accentuating the sounds of interest, of preventing load sounds which will annoy or injure the ears of the user while manipulating the pick-up head by hand. These large disturbances create pressure waves which are vented to the atmosphere through the resonant cavity rather than being directed to the ears of the user.

Referring to FIGS. 2 through 4, the structure of the pick-up head 11 for this example embodying the various aspects of the invention will be described. A base member 41 has a circular outer flange 43 threadedly attached thereto in a manner to securely hold the outer circumference of a circular diaphragm 13 thereto. Of course, the diaphragm 13 and flange 43 do not necessarily have to be circular in shape but this is the most convenient to manufacture.

The sound waves generated by vibration of the diaphragm 13 within a cavity 45 pass through an aperture 47 located in a wall of the cavity 45 opposite the diaphragm 13. The sound waves are then passed into a rigid tube 49 about which an end of the sound passage flexible tube 17 is tightly force fitted. The sound waves then travel through the hollow tube 17 to the ear pieces 19 and 21.

Upright rigid tubes 51 and 53 are also provided for force fitting there around of the flexible resonant cavity tubes 33 and 35. The tubes 51 and 53 are selectively connected for sound communication with the aperture 47 through a sliding valve 55. The valve 55 includes a passage 57 that is selectively positioned. In the position shown in FIG. 3A, neither of the tubes 51 or 53 are in sound communication with the aperture 47 or the sound passage 17. When the valve 55 is manually slid to one extreme position, as shown in FIG. 3B, the passage 57 connects the resonant cavity tube 33 with the aperture 47 and the sound passage 17. When the valve knob 55 is slid to an opposite extreme position, as shown in FIG. 3C, the valve passage 57 then connects the resonant cavity tube 35 to receive sound waves in air from the aperature 47 and the sound passage 17. Therefore, either the sound resonant cavity 33 or the sound resonant cavity 35, or neither, are selectively connected to the sound passage 17 at the rear of the sound pick-up head 11 in order to obtain the desired performance from the stethoscope for a given patient examination.

The valve 55 is held at one of its three stable positions by a ball detent 61 that is urged upward by a spring 63 captured within the base portion 41 of the sound pick-up head 11. A groove 65 is provided along the length of the valve slide 55 and contains three indentations along this length cooperatively shaped with the ball 61 for it to rest securely therein. The ball 61 is loose, being captured between the spring 63 and the valve slide 55. The three positive valve positions are thereby provided by these three indentations cooperating with the spring loaded ball 61. In construction the valve slide 55 is inserted into the base portion 41 with the ball 61 pushed down out of the way by compressing the spring 63. Once so installed, the valve slide 55 cannot be removed.

Referring to FIGS. 4A and 4B, the operation of the diaphragm 13 and probe 15 can be better understood. When the head of FIG. 4A is pushed against a patient 67 in a manner shown in FIG. 4B, the probe 15 and diaphragm 13 are pushed inward of the cavity 45, as clearly illustrated. Sound vibrations within the body 67 are then transmitted to the probe 15 which is in firm contact with the body and the diaphragm 13 is then caused to vibrate and set up those sound waves within the chamber 45 which are then communicated to a resonant cavity, if any, and the ear pieces 19 and 21 as described previously. The probe 15 is as sharp as possible on its outer end without being so sharp as to cause discomfort to the patient. It is desired that the probe contact be as small a point as possible so that the sound waves at that single point are detected. This is an improvement over a commonly used technique wherein a large area membrane or diaphragm contacts the patient's skin directly. The large area sound pick-up has a disadvantage of integrating the sound over the many points covered without providing a sharp, clear sound as results from use of the probe 15 as shown herein.

The diaphragm 13 is made to have maximum flexibility in its outer annular ring 69 while an inner circular portion 70 to which the probe 15 is firmly attached is less flexible. This is accomplished by the bends formed in the diaphragm 13 as best illustrated in the side cross-sectional view of FIG. 4A. The diaphragm 13 and probe 15 are preferably formed from a single piece of sheet metal or plastic. The result is that the entire inner circular portion 70 of the diaphragm 13 vibrates in accordance with the sounds picked up from the patient through the probe 15. This large vibrating area provides initial high volume sound within the chamber 45. Yet, the diaphragm is resilient enough in its outer portion 69 to enable it to urge the probe 15 firmly against the skin of a patient 67 as shown in FIG. 4B. The diaphragm 13 is positioned a distance inward of the lip 71 so that, for a given length probe 15 and shape of the diaphragm 13, the probe 15 is firmly held against the patient 67 when in use. The lip 71 also provides a firm seating of the pick-up head 11 against the patient 67 which aids in preventing any movement of the head 11 during an examination and reduces the influence of extraneous noises and vibrations in addition to the sound desired to be detected by the instrument.

A plurality of openings 73 and 75 are provided through the flange 43. These openings prevent a vacuum from forming between the skin of the patient 67 and the diaphragm 13 when the pick-up head is in use. Such a vacuum would be undesirable since it would interfere with free movement of the diaphragm 13 in accordance with the sounds picked up from the patient 67.

Referring to FIG. 5, another embodiment of the present invention is illustrated wherein a resonant tube and valve are added to an existing stethoscope. A standard pick-up head 81 is employed, as are usual ear pieces 19' and 21', connected respectively to metal tubes 27' and 29'. (The prime ['] shows the equivalent parts to that of the embodiment of FIG. 1) Rather than a simple tube connected between the pick-up head 81 and the ear tubes 27' and 29', as is done with existing stethoscopes, a tube structure 83 according to the present invention is substituted. This structure includes an entrance tube portion 85 connected to receive sound vibrations from the pick-up head 81. A mechanical valve 87 receives the sound waves through the tube 85 and directs them either into a tube 89 or into both the tube 89 and a resonant cavity tube 91. The tube 89 provides a closed sound path to the ear piece tubes 27' and 29'. The tube 91 is open to the atmosphere, being mechanically connected to the tube 89 for convenience and appearance.

FIGS. 6A and 6B illustrate in enlarged view operation of the valve 87 of FIG. 5. A case 95 has a plunger 97 therein that is sealed to the inside of the case 95. Both the inside surface of the case 95 and the outside surface of the plunger 97 are preferably cylindrical in shape and of mating sizes within close tolerances. A spring 99 within the cylindrical cavity of the case 95 urges the plunger 97 away from a plugged end 101 of the case and against the other end. A button 103 attached to the plunger 97 extends outward of the other end of the case 95 and when pushed urges the plunger 97 from a rest position of FIG. 6A to an intermediate position of FIG. 6B.

The valve 87 of FIGS. 5, 6A and 6B is normally positioned in the specific embodiment being described so that the resonant cavity 91 is connected into the sound transmission passage provided by the tubes 85 and 89. The button 103 of the valve 87 is made just long enough so that when fully depressed, in a manner shown in FIG. 6B, the plunger 97 closes off the resonant cavity sound passage 91 and converts the structure of FIG. 5 into a normally operating stethoscope. However, with the resonant cavity normally connected with the valve at rest as shown in FIGS. 5 and 6A, the stethoscope is set to respond with the loudest sounds possible. Also, with the resonant chamber tube 91 normally connected, any bumping or other damaging noise caused by handling of the pick-up 81 as it is moved to and from a patient are prevented from reaching the ears of the user by venting them to the atmosphere through the open resonant tube 91.

Rather than the pick-up head 81 of the standard commercial variety, the improved pick-up head 11, as described with respect to FIGS. 1, 4A and 4B, (but without the valve structure) can be substituted in the embodiment of FIGS. 5, 6A and 6B. Such a combination provides the advantages of both the resonant tubes and the probe sound pick-up in a single structure. It may be of some advantage to users of the improved stethoscope of the present invention to have the valve structure (if one is used) removed from the pick-up head a few inches along the sound transmission tube.

It has also been discovered as part of the present invention that the connection of both resonant tubes 33 and 35 to the sound chamber 45 (FIG. 1) results in an instrument that allows the user to clearly and loudly hear high frequencies associated with an improperly operating heart valve of a patient. Presently, only electronic instruments are capable of allowing a doctor to listen to these sounds. To make possible this added feature, the valve of the FIGS. 1-4 embodiment can be modified (not shown) to permit both of the tubes 33 and 35 to be connected in addition to the operator choices provided by the valve as shown.

Such a valve structure is illustrated in FIG. 7. The valve 87' is designed to be substituted for the valve 87 of the embodiment of FIGS. 5, 6A and 6B. A second resonant tube 90 is selectively connectable to the sound path 85' by manual operation of a second plunger 98 through an outwardly extending pushbutton 100. The two pushbuttons 103' and 100 are conveniently located on opposite sides of the valve case 95' so the operator can depress one or both with fingers on a single hand. When neither button is depressed, both resonant tubes 91' and 90 are operably connected into the sound transmission path 85'. When the button 100 only is depressed, the tube 90 is cut-off and only the tube 91' is connected. When the button 103' only is depressed, the tube 91' is cut-off and only the tube 90 is connected. When both buttons 100 and 103' are depressed at the same time, the sound passes straight through from the tube 85' to the tube 89' without either resonant tubes being connected.

The tubes 91 and 91' of the FIGS. 5-7 embodiment correspond in length to the larger resonant tube 35 of the FIG. 1 embodiment. The tube 90 of FIG. 7 is open ended and of the shorter length of the tube 33 of FIG. 1.

Referring to FIG. 8, a variation of the embodiment of FIGS. 1 through 4 is illustrated. The diaphragm 13' and probe 15' have the same structure, as does the cap 71' and the air vent 73'. A different shaped pick-up case 107 is provided, however, in order to make room for a coiled rigid or flexible resonant tube 109 that is placed therein. One end of the tube 109 opens into the cavity 45' in which the sound waves are generated by vibration of the membrane 13'. An opposite end 111 of the coiled tube 109 is open. The rigid tube 49' is also connected to the chamber 45' and communicates the sound generated therein through a tube 113 to normal ear pieces (not shown in FIG. 8). The embodiment of FIG. 8 shows a pick-up head which can replace the pick-up head of a standard stethoscope without having to change anything else. No valve is shown in the embodiment of FIG. 8 to selectively close off the resonant tube 109 but one could easily be added. Also, a second resonant tube could be provided within a somewhat larger pick-up head case 107, if desired, and a valve could be provided for selectively connecting one chamber or the other with the sound transmission passage of the stethoscope.

Although the various aspects of the present invention have been described with respect to specific structural examples of stethoscopes emboding such inventions, it will be understood that equivalent various structures are possible and that the invention protected is within the full scope of the appended claims.

What is claimed is:

1. In a stethoscope having a sound pick-up head and at least one ear piece that are connected at opposite ends of an enclosed sound transmission passage therebetween, the improvement comprising an elongated resonant cavity of a given volume connected at one end to said enclosed sound transmission passage in the vicinity of said pick-up head and opened to the atmosphere at its other end, thereby allowing sound waves from said pick-up head to simultaneously pass through both the resonant cavity and the enclosed passage, whereby said resonant cavity causes sound frequencies within a given resonant frequency range to be amplified between the pick-up head and said ear piece.

2. The improved stethoscope according to claim 1 wherein said enclosed passage includes a length of hollow tube and further wherein said resonant cavity includes a second length of hollow tube that is open to the atmosphere at its free end.

3. The improved stethoscope according to claim 1 which additionally comprises a valve manually operable to selectively open or close the connection of said resonant cavity with said sound transmission passage.

4. The improved stethoscope according to claim 3 wherein said valve is formed as part of said pick-up head as a unitary structure.

5. The improved stethoscope according to claim 3 wherein said valve is positioned in the path of said enclosed sound transmission passage as an element physically separate from the pick-up head but connected therewith through a portion of said sound passage.

6. The improved stethoscope according to either of claims 3 or 5 wherein said valve comprises a structure biased to normally connect the resonant cavity to the sound transmission passage until manually operated to close off the resonant cavity.

7. The improved stethoscope according to claim 1 wherein said resonant cavity comprises a tube open at one end and connected at another end to said sound transmission passage, said tube being coiled within said pick-up head.

8. The stethoscope according to claim 1 wherein the improvement additionally comprises a second elongated resonant cavity having a volume significantly different than that of said resonant cavity, said second resonant cavity also being connected at one end to the enclosed sound transmission passage in the vicinity of said pick-up head and being opened to the atmosphere at its other end, said improvement further comprising a valve connected to said sound passage in a manner to permit selective connection of either said cavity or said second cavity to said sound passage, whereby said second resonant cavity causes sound frequencies within a second given resonant frequency range to be amplified and said valve permits selection of said given or said second frequency range for amplification.

9. The stethoscope according to claim 8 wherein each of the resonant cavities include different lengths of tubing as major components thereof, whereby the length of tubing for one resonant cavity can be designed to maximize amplification for heart sounds and the other for lung sounds.

10. The improved stethoscope according to claim 8 wherein said valve is mounted on a back surface of said sound pick-up, said valve being manually operable to connect one or the other or neither of the resonant cavities to said sound transmission passage.

11. The stethoscope according to claim 1 which additionally includes an improved pick-up head which comprises:
a cup-like structure opening outward in a lip and having an opposite generally closed surface with an opening that connects into said sound transmission passage,
a diaphragm attached within said cup-like structure a given distance from its said lip,
a probe having a length greather than said given distance connected as part of said diaphragm and extending outward of said cup-like structure, whereby a body to be monitored is contacted by said probe and cup-like structure lip and sound vibrations are generated within said enclosed passage according to sound vibrations within the monitored body, said probe being brought to a blunt point of small dimensions, whereby sound is picked up from a body at substantially a point thereon, thereby making the sound pick-up clear and without interference from independent sound vibrations existing in other points of the body, and
an air passage through said cup-like structure in a location between the connection of the diaphragm and the outer lip, thereby to permit the diaphragm to move freely without air pressure impedance, 12. The improved stethoscope according to claim 11 wherein said diaphragm is circular in shape and attached around its circumference to an inside surface of said cup-like structure, said diaphragm being flexible for a portion around its outside adjacent its circumference, an adjoining center portion of said diaphragm being rigid and attached to said probe.

13. The improved stethoscope according to claim 8 wherein said valve is further characterized by permitting simultaneous connection of both said elongated resonant cavities to the enclosed sound transmission passage, whereby yet another frequency range is amplified that is higher than those of either of said elongated resonant cavities when connected alone.

14. The improved stethoscope according to claim 13 wherein said valve comprises separately operable valves that independently control whether each of the two elongated resonant cavities is opened or closed to the enclosed sound transmission passage, each of said separately operable valves being resiliently urged to an open position.

15. In a stethoscope having a sound pick-up head and at least one ear piece that are connected at opposite ends of an enclosed sound transmission passage therebetween, the improvement comprising mechanical means including an open ended cavity of a given volume connected to said enclosed sound transmission passage adjacent said pick-up head in a manner that sound from the pick-up head simultaneously travels to the ear piece and said cavity, thereby amplifying at said ear piece a given frequency range of sounds detected at said pick-up head, said given frequency range being dependent upon the volume of said cavity, said volume being selected to maximize the amplitude of sounds made by a certain function of the body that are in a defineable frequency range, such as those of the heart or lungs.

16. In a stethoscope having a sound pick-up head and at least one ear piece that are connected at opposite ends of a hollow air sound transmission passage, an improved sound pick-up head comprising:
a shell having first and second openings, said first opening being much larger than said second opening,
means connecting said second opening to said sound transmission passage,
a resilient diaphragm extending across said first opening and held at its edges to said shell,
a probe of a given length firmly attached to said diaphragm in a middle portion thereof and shaped into a blunt point to be pushed against a patient's skin, thereby to pick up sound from a body at substantially a point thereon,
a positioning stop attached as part of said shell and extending in the direction of said probe a distance from said diaphragm that is less than said given length of the probe, thereby to limit the force of the point applied to the patient through the resiliency of the diaphragm and provide a firm surface for stabilizing the head against the patient, and
at least one air passage provided through said shell on the probe side of said diaphragm, thereby to permit the diaphragm to move freely without air pressure impedance when the stops are held against a patient's skin.

17. The improved stethoscope according to claim 16 wherein the portion of said diaphragm immediately surrounding said probe is rigid and further wherein a portion of said diaphragm surrounding said rigid portion and connecting with said shell is flexible.

18. The improved stethoscope according to claim 16 wherein said pick-up head additionally comprises a valve attached to an outside surface of said shell, said valve constructed to selectively connect either of a first or second outlet port to said second shell opening.

19. The improved stethoscope according to claim 18 which additionally comprises first and second segments of hollow tubing of significantly different lengths, one end of one length of tubing being connected to said first port and one end of the second length of tubing being connected to said second port, the opposite ends of each of said first and second lengths of tubing being open to the atmosphere.

20. A method of monitoring sounds internally generated in a body, such as heart and lung sounds, comprising the steps of:
holding a bluntly pointed probe against the outside of said body, whereby it vibrates according to the sound vibrations within said body,
generating sound waves in an enclosed air chamber from the vibrating probe through a diaphragm that is attached to the probe,
communicating said sound waves to a sound detector, such as a human ear, from the enclosed air chamber, and
simultaneously communicating said sound waves from the enclosed air chamber to one end of a hollow resonant tube that is open to the atmosphere at its other end, whereby the detected sounds are amplified.

21. For a stethoscope having a sound pick-up head, at least one ear piece and a flexible tube for carrying sound from the pick-up head to said at least one ear piece, the improvement comprising:
 a valve connected into said tube at a position near the pick-up head for controllably connecting a port thereto in response to manual actuation, and
 a second length of tube with one end connected to said port and another end open, thereby to provide a resonant chamber that is selectively connected with the sound carrying tube.

22. The stethoscope improvement according to claim 21 wherein said valve is biased to normally provide for sound connection between said sound carrying tube and said second tube, and includes means responsive to manual actuation to close off said second length of tube at its connection with said sound carrying tube.

23. For a stethoscope having a sound pick-up head, at least one ear piece and a flexible tube for carrying sound from the pick-up head to said at least one ear piece, the improvement comprising:
 a valve connected into said tube at a position near the pick-up head or controllably connecting either of two ports or both thereto in response to manual actuation,
 a second length of flexible tube with one end connected to one of said ports and another end open,
 a third length of flexible tube with one end connected to the other of said ports and another end open, said second length of tube being significantly longer than said third length of tube.

24. A method of monitoring sounds internally generated in a biological body, such as heart and lung sounds, comprising the steps of:
 providing a structure of a resilient diaphragm held across a circular opening but recessed a distance into said opening from a circular edge, said diaphragm carrying a probe attached to its center and shaped into a blunt point extending beyond said opening edge,
 holding said structure against a biological body with said circular edge contacting skin of the body and with the probe point indenting the skin and causing the diaphragm to be pushed further into the circular opening,
 providing an air passage through the structure forming the circular opening at a location between the circular edge and the diaphragm, thereby to permit the diaphragm to move freely without air pressure impedance when the circular edge is held firmly against the skin, and
 communicating the sound vibrations from a side of the diaphragm opposite the probe to a sound detector such as an ear, whereby sound is detected from a substantial point of said biological body with the result of the sound being clear without interference from independent sounds existing at other points of the body.

* * * * *